United States Patent [19]

Winnie

[11] 4,040,427
[45] Aug. 9, 1977

[54] CATHETER SUPPORT ASSEMBLY

[75] Inventor: Alon P. Winnie, Wilmette, Ill.

[73] Assignee: The Kendall Company, Boston, Mass.

[21] Appl. No.: 672,590

[22] Filed: Apr. 1, 1976

[51] Int. Cl.² .................................... A61M 25/02
[52] U.S. Cl. .................... 128/348; 128/DIG. 26; 128/133
[58] Field of Search ................ 128/348–351, 128/132–133, DIG. 26, 215; 5/91

[56] References Cited

U.S. PATENT DOCUMENTS

| 2,250,325 | 7/1941 | Barnes | 5/370 X |
|---|---|---|---|
| 2,463,400 | 3/1949 | Lowe | 128/215 |
| 3,138,158 | 6/1964 | Gordon et al. | 128/133 |
| 3,319,272 | 5/1967 | Eller | 5/338 |
| 3,568,679 | 3/1971 | Reif | 128/133 X |
| 3,696,920 | 10/1972 | Lahay | 206/63.2 R |

*Primary Examiner*—Dalton L. Truluck
*Attorney, Agent, or Firm*—Powell L. Sprunger

[57] ABSTRACT

A support assembly for a catheter extending from a patient's body comprising, a support member of compressible foam material having a slot extending from an outer edge of the support member, and adhesive on an inner surface for securing the support member to the patient's body with the catheter received in the slot. The support member has a sufficient thickness to cushion the patient's body and prevent kinking of the catheter when the patient reclines on the support member.

4 Claims, 6 Drawing Figures

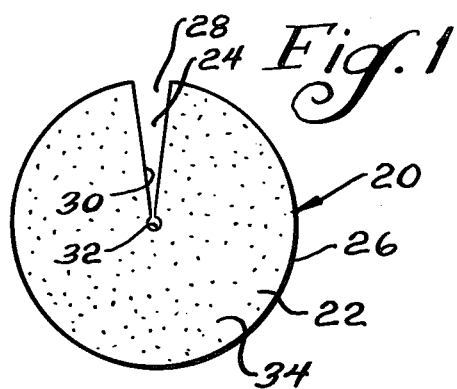
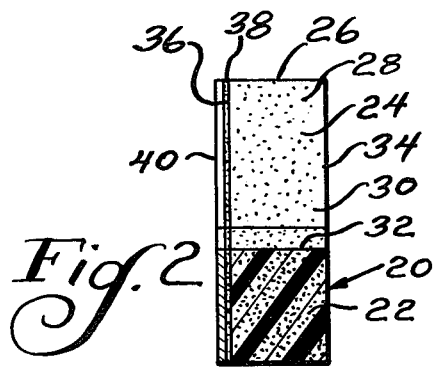
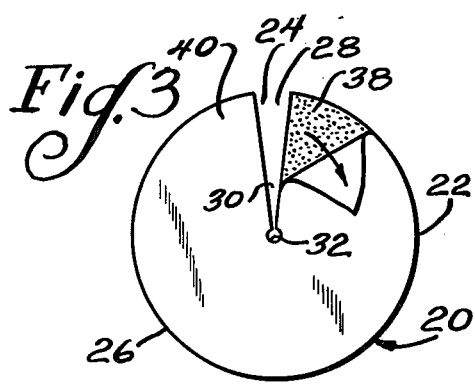
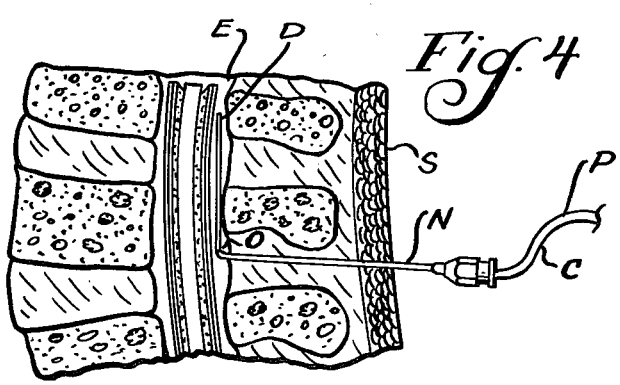
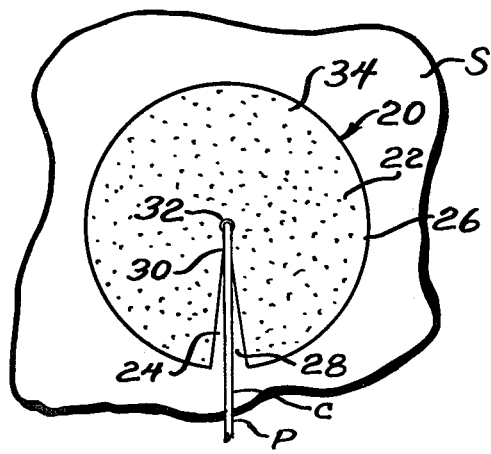
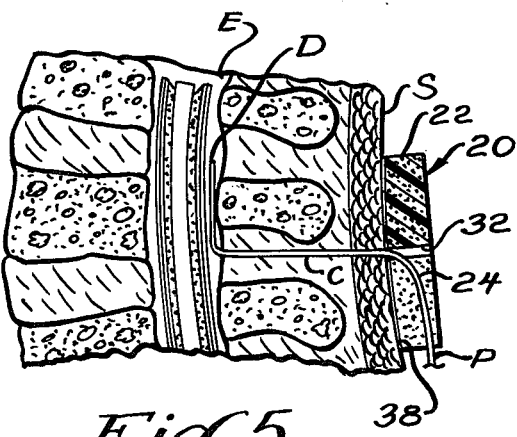

CATHETER SUPPORT ASSEMBLY

BACKGROUND OF THE INVENTION

The present invention relates to catheter assemblies.

During certain medical procedures a distal end of a catheter is positioned inside the patient's body, with a proximal end portion of the catheter extending outside the patient's body. The catheter may remain in this position for relatively short or for extended lengths of time, and the catheter may be used to drain fluids from the patient's body or inject fluids into the patient's body at a location where the patient reclines on the catheter. For example, in a continuous epidural or caudal anesthesia procedure an anesthetic solution is periodically injected through a catheter into the epidural space or sacral canal of the patient, respectively, while the patient may recline on his back over the catheter during a surgical procedure. Thus, it is necessary to prevent kinking of the catheter during the procedure, else the lumen of the catheter may become closed, preventing further injection of the anesthetic solution.

SUMMARY OF THE INVENTION

A principal feature of the present invention is the provision of an assembly of simplified construction for supporting a catheter during a surgical procedure.

The support assembly of the present invention comprises, a support member of compressible foam material having a slot extending from an outer edge of the support member, and pressure- sensitive adhesive on an inner surface.

A feature of the present invention is that the support member may be secured to the patient's body by the adhesive after placement of the catheter with the catheter received in the slot.

Another feature of the invention is that the support member has a sufficient thickness to prevent kinking of the catheter when the patient reclines on the support member.

Thus, a feature of the invention is that the support member may be readily placed at its support position, and the support member minimizes the possibility of catheter blockage during subsequent use of the catheter.

Further features will become more fully apparent in the following description of the embodiments of this invention and from the appended claims.

DESCRIPTION OF THE DRAWINGS

In the drawings:

FIG. 1 is a front plan view of a support member of the present invention;

FIG. 2 is a sectional view taken substantially as indicated along the line 2—2 of FIG. 1;

FIG. 3 is a back plan view of the support member of FIG. 1 showing a release sheet as partially peeled away from adhesive on the support member;

FIG. 4 is a diagrammatic sectional view of a patient's body illustrating a step in the placement of a catheter for performing a continuous epidural anesthesia procedure;

FIG. 5 is a diagrammatic sectional view of the patient's body illustrating the support member of the present invention as placed on the patient's body to prevent kinking of the catheter during the continuous epidural anesthesia procedure; and FIG. 6 is a plan view illustrating the support member of FIG. 5 as secured to the patient's body.

DESCRIPTION OF THE PREFERRED EMBODIMENTS

Although for convenience the support assembly of the present invention will be described primarily in connection with a continuous epidural anesthesia procedure, it will be understood that the assembly may be used for other suitable procedures. For example, the support assembly of the present invention may be used in connection with a continuous caudal anesthesia procedure, or for draining body fluids from a patient, as desired.

Referring now to FIGS. 1-3, there is shown a support assembly generally designated 20 having a support member 22 which is made from a relatively soft, flexible, and compressible foam material, such as urethane foam. The support member 22 may have a generally cylindrical shape, as shown, and has a tapered slot or slot means 24 of generally triangular configuration extending through the thickness of the support member between outer and inner surfaces 34 and 36, respectively, of the support member, and extending from an inner central portion of the support member to an outer edge 26 of the support member 22. The slot 24 has an outer portion 28 of large diameter than the outside diameter of a catheter to be received in the slot, and an inner portion 30 which may be smaller than the outside diameter of the catheter. As shown, the apex 32 of the slot 24 may be located at the center of the support member 22.

The support member 22 has a coating of pressure-sensitive adhesive 38 on its inner surface 36, and a release sheet 40 releasably attached to and covering the adhesive 38 on the support member 22. With reference to FIG. 3, the release sheet 40 may be removed from the adhesive 38 in order to expose the adhesive and secure the support member 22 on the body of the patient, as will be described below.

The use of the support assembly of the present invention for a spinal epidural anesthesia procedure is described in connection with FIG. 4-6. As shown in FIG. 4, a needle N is positioned in the patient's body according to known procedures with an opening O of the needle N being located in the epidural space E of the patient. A catheter C is advanced through the needle N and through the needle opening O unitl a distal end D of the catheter C is located in the epidural space E with a proximal end portion P of the catheter C being located outside the patient's body. The needle N is then removed from the patient's body and from the proximal end portion P of the catheter C, while the distal end D of the catheter C remains in place in the patient's body. Next, the proximal end portion P of the catheter C is connected to a syringe (not shown) which contains an anesthetic solution, and the syringe is utilized to periodically inject the anesthetic solution through the catheter C into the epidural space E throughout the duration of a surgical procedure. However, if the patient reclines on his back over the catheter during the surgical procedure, it has been found that the patient's weight may cause kinking and blockage of the catheter. Thus, if further anesthesia is required during the surgical procedure must be interrupted in order to reposition the patient and open the catheter for injection of further anesthetic solution.

According to the present invention, as illustrated in FIGS. 5 and 6, after placement of the catheter and after removal of the needle N from the catheter, the release sheet is removed from the adhesive 38 of the support member 22, and the support member is attached to the patient's body by the adhesive 38 with the proximal end portion P of the catheter C being received in the slot 24 of the support member. The support member 22 then serves as a cushion about the site where the catheter enters the patient's body. The support member has a sufficient thickness between its outer and inner surfaces 34 and 36, respectively, to prevent kinking of the catheter when the patient reclines on the support member during the surgical procedure. Thus, the support member 22 assures that the catheter is maintained with its lumen open during the surgical procedure, in order that the anesthetic solution may be injected into the epidural space without difficulty at selected intervals during the surgical procedure.

The foregoing detailed description is given for clearness of understanding only, and no unnecessary limitations should be understood therefrom, as modifications will be obvious to those skilled in the art.

What is claimed is:

1. A catheter support assembly, comprising:
   a catheter having a distal end for placement in a patient's body, and a proximal end portion extending outside the patient's body when the catheter is placed;
   a support member of relatively soft and compressible foam material and having an inner surface for facing the patient's body, an outer surface facing away from the patient's body, and a slot extending between said inner and outer surfaces and extending between an outer edge of the support member toward a central portion of the support member, a pressure-sensitive adhesive on said inner surface, and a release sheet releasably covering said adhesive, said support member being secured to the patient's body by said adhesive with said proximal end portion of the catheter located in said slot, said support member having a sufficient thickness between said inner and outer surfaces to cushion the patient's body and prevent kinking of the catheter when the patient reclines on the support member.

2. The catheter assembly of claim 1 wherein said slot is tapered from said outer edge of the support toward said central portion of the support member.

3. The catheter assembly of claim 1 wherein said support member has a generally cylindrical shape.

4. The catheter assembly of claim 3 wherein said slot comprises a generally triangular shaped cut-out of the support member having its apex located generally centrally in the support member.

* * * * *

UNITED STATES PATENT AND TRADEMARK OFFICE
CERTIFICATE OF CORRECTION

PATENT NO. : 4,040,427
DATED : August 9, 1977
INVENTOR(S) : Alon P. Winnie

It is certified that error appears in the above-identified patent and that said Letters Patent are hereby corrected as shown below:

Column 2, line 25, "large" should be -- larger -- .

Column 2, line 63, after "dure" add -- and if the catheter is blocked, the surgical procedure --.

Signed and Sealed this

Twenty-seventh Day of December 1977

[SEAL]

Attest:

RUTH C. MASON
*Attesting Officer*

LUTRELLE F. PARKER
*Acting Commissioner of Patents and Trademarks*